(12) United States Patent
Dobbs

(10) Patent No.: US 6,748,043 B1
(45) Date of Patent: Jun. 8, 2004

(54) METHOD AND APPARATUS FOR STABILIZING THE MEASUREMENT OF CT NUMBERS

(75) Inventor: John M. Dobbs, Hamilton, MA (US)

(73) Assignee: Analogic Corporation, Peabody, MA (US)

(*) Notice: Subject to any disclaimer, the term of this patent is extended or adjusted under 35 U.S.C. 154(b) by 137 days.

(21) Appl. No.: 09/982,192

(22) Filed: Oct. 18, 2001

Related U.S. Application Data
(60) Provisional application No. 60/241,696, filed on Oct. 19, 2000.

(51) Int. Cl.[7] .............................................. G01N 23/00
(52) U.S. Cl. ............................................ 378/4; 378/16
(58) Field of Search ........................ 378/4, 18, 5, 901, 378/54, 98.7, 111, 109, 110, 101, 19, 16

(56) References Cited

U.S. PATENT DOCUMENTS

| | | | | |
|---|---|---|---|---|
| 4,105,922 A | * | 8/1978 | Lambert et al. ............. | 382/131 |
| 4,361,900 A | * | 11/1982 | Siedband ..................... | 378/98 |
| 5,022,063 A | * | 6/1991 | Yokouchi et al. ............. | 378/99 |
| 5,822,393 A | * | 10/1998 | Popescu ...................... | 378/108 |

* cited by examiner

Primary Examiner—David V. Bruce
Assistant Examiner—Irakli Kiknadze
(74) Attorney, Agent, or Firm—McDermott, Will & Emery

(57) ABSTRACT

An apparatus and method is provided for stabilizing CT number calculations by a CT system against fluctuations in the x-ray source voltage due to voltage source drift. A voltage reference level is established, by adjusting the voltage to the value which yields the correct CT number for a sample having a known CT number value. The x-ray energy spectrum measured by a kV meter is used to maintain the voltage constant at this reference level. The kV meter has a principal detector that generates a first intensity magnitude of the x-rays, and an auxiliary detector that generates a second intensity magnitude. The auxiliary detector includes an absorber that preferentially absorbs x-ray photons having a relatively low energy. A feedback controller provides to the voltage source a voltage control signal, which is continuously adjusted as a function of the first and second intensity magnitudes, so as to maintain the voltage constant at the reference level.

20 Claims, 5 Drawing Sheets ns. The CT number for bone is from about 800 to about 1400, whereas metals often have CT numbers in excess of 2000.

METHOD AND APPARATUS FOR STABILIZING THE MEASUREMENT OF CT NUMBERS

CROSS-REFERENCE TO RELATED APPLICATIONS

This application claims the benefit of priority from U.S. Provisional Application No. 60/241,696, filed Oct. 19, 2000.

STATEMENT REGARDING FEDERALLY SPONSORED RESEARCH

Not Applicable

REFERENCE TO MICROFICHE APPENDIX

Not Applicable

FIELD OF THE INVENTION

This invention relates to the measurement of CT numbers, and more particularly to a method and apparatus for stabilizing the measurement of CT numbers.

BACKGROUND OF THE INVENTION

X-ray computed tomography (CT) allows an image of the internal structure of a target object to be generated, one cross-sectional slice at a time, by irradiating the target object with x-rays. The target object may be an anatomical region of a patient, such as the head or the chest. In this case, CT allows structures inside the human body, such as blood clots and tumors, to be visualized accurately without invasive surgery. Many other applications have been found for CT, including but not limited to, the detection of explosives in luggage and the analysis of fluids in petroleum engineering.

In a CT system, x-rays emitted from an x-ray source pass through a slice of the target object, and are detected by a detection system. The slice is irradiated from many different directions, for example by rotating the x-ray source and detector around a patient so that each revolution of the x-ray source and detector produces a scan of a single slice of the target region. In spiral (or helical) CT systems, the x-ray source rotates continuously as the patient is moved through the x-ray scan field, so that a continuous set of data is obtained for the entire region scanned.

The detection system measures the intensity of the x-ray beam that has been transmitted through a slice of the target object. The material within a slice irradiated by an x-ray beam attenuates the beam by absorbing and/or scattering the x-rays. The detection system generates detection signals indicative of the attenuated intensities of the x-rays that have traversed the slice, digitizes them, and transmits the digitized detection signals to a computer.

The computer implements image processing techniques, known in the art, to generate an image of the target object, slice by slice. Each slice is viewed as being composed of a plurality of individual volume elements. Information regarding the total attenuation of each of a very large number of x-ray beams, which traverse the patient in essentially all directions and at all radii from the center of the field of view, is used to determine the density and structure of each volume element. Each volume element is characterized by a numerical value, referred to as the CT number, which represents the x-ray attenuation characteristics of the element. CT numbers are conventionally scaled relative to the x-ray attenuation coefficient of pure water, which is assigned a CT number equal to 0 under the Hounsfield scale that ranges from low density (about −1000) to high density (about +3095). The CT number of a material thus represents the attenuation coefficient of the material relative to the attenuation coefficient (0) of pure water. Soft tissues commonly have CT numbers in the range from about −100 to about 200. The CT number for bone is from about 800 to about 1400, whereas metals often have CT numbers in excess of 2000.

A CT image is generated as a map or distribution within the target object of such arrays of CT numbers. The reconstruction of an image by a CT system thus requires an accurate measurement of x-ray attenuations, and an accurate determination of CT numbers. Many industrial applications of CT require that the CT number of a material be determined with great precision and accuracy. As one example, part of the recognition algorithm used in CT scanning for the detection of explosives refers to the CT numbers of known explosives in order to recognize explosives within an object, such as luggage.

The calculated CT numbers are related to the energy of the x-ray beam, which in turn is related to the voltage provided to the x-ray source that generates the x-rays. The calculated CT numbers thus depend strongly on the voltage provided by the power supply to the x-ray source. The only other parameters that affect the CT number are those that define the physical geometry of the CT scanner and its inherent x-ray absorption, which can be maintained constant over long periods of time. Any fluctuations in the x-ray source voltage thus impair the accuracy and stability of CT number measurements by a CT system. These fluctuations are typically caused by voltage source drift, for example due to the drift of resistor values with time. A CT system must therefore have a very stable voltage source connected to the x-ray source, in order for accurate and stable measurements of CT numbers to be possible. In order to reliably make about 0.1% measurements of CT numbers for many years, the voltage provided to the x-ray source must be stable to about 0.03%, for many years.

Stability in x-ray source voltage is very difficult and expensive to obtain in practice, because very stable electronic components are typically not suitable for high voltage applications, such as the generation of x-rays. Indeed, the task of testing the electronic components of a CT system, and proving that they are stable over time and over possible changes in the environment, is very expensive and difficult. It is therefore desirable to provide a CT system which has inherently stable components that do not require such testing.

It is an object of this invention to provide a low-cost method and apparatus for allowing a CT system to determine CT numbers with improved accuracy and stability. It is another object to provide a method and apparatus for maintaining the determination of CT numbers by a CT system stable against fluctuations in the voltage provided to the x-ray source.

SUMMARY OF THE INVENTION

The invention relates to a method and apparatus for stabilizing the measurement of CT numbers against fluctuations in the x-ray source voltage. In the present invention, CT number measurements are stabilized by detecting the fluctuations in the x-ray source voltage or equivalently, in the x-ray energy, using x-ray intensity magnitudes that are measured by a device, henceforth called a kV meter.

A CT system in accord with the present invention includes an x-ray source for emitting x-rays in response to an accelerating voltage provided by a voltage source. A detection system, preferably including an array of detectors, detects x-rays emitted by the x-ray source and transmitted through a target object. The CT system further includes an image processor for reconstructing a CT image of the target object. The image processor calculates the CT numbers of the target object from the measurements of the attenuated intensities of x-rays transmitted through the target object and detected by the detector system.

The CT system also includes a kV meter. In the present invention, the kV meter includes a principal detector and an auxiliary detector. The auxiliary detector is covered with an absorber that removes a large fraction of the lower-energy x-ray photons in the incident x-ray beam. The ratio between a first x-ray intensity magnitude measured by the principal detector, and a second x-ray intensity magnitude measured by the auxiliary detector, is a strong, stable function of the voltage supplied to the x-ray source. This ratio, or the corresponding voltage, serves as a reference level for the stabilization of the power source for subsequent CT number measurements by the CT system.

As a calibration, the CT system calculates the CT number of a sample having a known CT number value. The sample may be a vessel containing water, by way of example. The voltage supplied by the voltage source is adjusted to the value which yields the correct, known CT number value for the sample. The kV meter measures the x-ray intensities from the principal and the auxiliary detector, and determines from them the magnitude of the voltage supplied to the x-ray source, when the CT number of the sample, as calculated by the CT system, matches the known CT number.

The CT system includes a controller, which provides a voltage control signal to the voltage source. The controller continuously adjusts the voltage control signal so as to maintain the voltage constant at the reference level established during calibration. Equivalently, the controller adaptively adjusts the voltage control signal based on a known and measurable function of the first and second intensity magnitudes generated by the kV meter, such as the measured ratio of the first and second intensity magnitudes as referred to above. In a preferred embodiment of the invention, the controller uses the measured ratio or other known function as a sensitive way of detecting any fluctuation in voltage from the reference level, and adaptively adjusts the control signal based on the measured ratio or other known function of the intensity magnitudes. Undesirable fluctuations in voltage are thereby prevented, and the measurement of CT numbers is stabilized against such fluctuations.

A method is provided for stabilizing the measurement of CT numbers by a CT system having an x-ray source for emitting x-rays in response to a voltage supplied by a voltage source. The method includes calibrating the CT system, initially. During calibration, the CT number of a sample (for example a water sample) having a known CT number value is calculated. The method includes adjusting the x-ray source voltage of the CT system, until the calculated value of the CT number of the sample matches the known CT number value. The magnitude of this x-ray source voltage then serves as a reference level for feedback control.

The method includes using the x-ray spectrum measured by a kV meter to keep the voltage constant against fluctuations from the reference level, caused by voltage source drift. The method includes using a principal detector, and an auxiliary detector including an absorber that preferentially absorbs x-ray photons having a relatively low energy. The method includes measuring a first x-ray intensity magnitude using the principal detector, and measuring a second x-ray intensity magnitude using the auxiliary detector.

The method includes providing a voltage control signal to the voltage source, during subsequent CT number measurements by the CT system. The method includes continually adjusting the voltage control signal as a function of the ratio (or other measurable relationship) between the first and second intensity magnitudes. In this way, the x-ray source voltage is maintained substantially constant at the reference level established during calibration, thereby substantially reducing in the CT system a variation in the measured values of CT numbers caused by voltage source drift.

DETAILED DESCRIPTION

Figure 1:
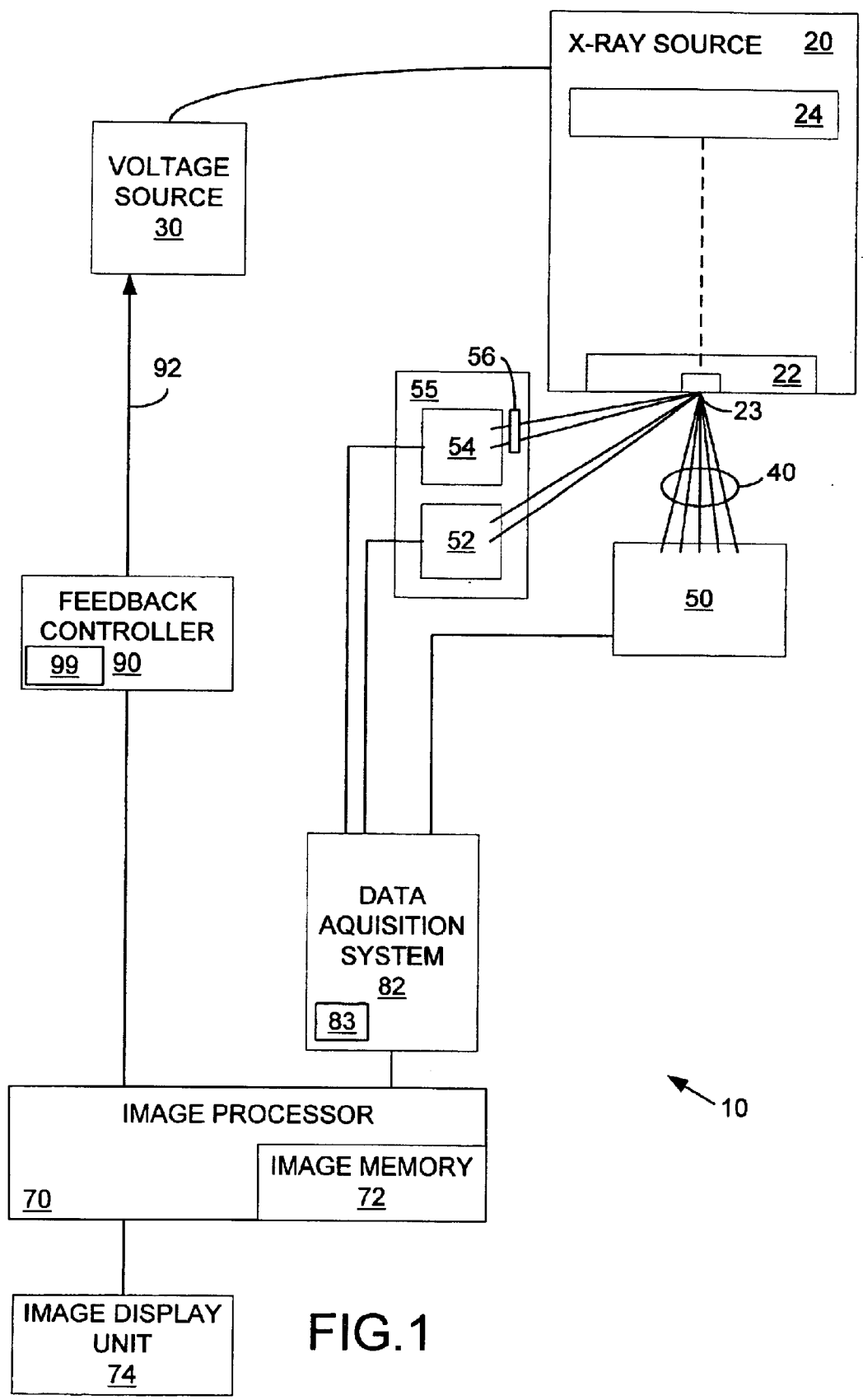
FIG. 1 provides a schematic overview of a CT system constructed in accordance with the present invention.

The present invention provides a low cost method and apparatus for stabilizing the measurement of CT numbers against fluctuations in the x-ray source voltage, caused for example by voltage source drift. FIG. 1 provides a schematic overview of a CT system 10 constructed in accordance with one embodiment of the present invention. In overview, the CT system 10 includes an x-ray source 20 that emits x-rays in response to a voltage supplied by a voltage source 30, and a detection system 50 for detecting the x-rays emitted by the x-ray source 20 and transmitted through a slice 40 of a target object. The CT system 10 also includes a kV meter 55, a data acquisition system 82, and an image processor 70. The CT system 10 further includes a feedback controller 90 that includes a processing unit 99.

Referring to each element in more detail, the x-ray source 20 may be a conventional x-ray tube, in which x-rays are produced by accelerating electrons through an electric field. The x-ray source 20 includes an electron source 24 for generating electrons, and a target 22 containing x-ray emissive material adapted to emit x-rays in response to incident accelerated electrons. The accelerating electric field is established by means of a voltage provided to the x-ray source 20 by a voltage source 30, typically a high voltage power supply. X-rays are generated due to the interaction of the accelerated electrons with the electrons and the nuclei that make up the atoms of the target material. The generated x-rays radiate in all directions from a spot 23 on the target 22 where the electron-target collisions take place, but typically are collimated before irradiating a target object. The spot 23 is commonly called the focal spot.

A highly collimated beam of x-rays, generated by the x-ray source 20, impinges upon a slice 40 of the target object, and passes through the material in the slice. The material within the slice 40 attenuates the x-ray beam, because of Compton scattering, and because of the photoelectric absorption of the x-rays by the atoms that constitute the slice. The attenuated intensities of the x-rays that have traversed the slice 40 of the object are detected by the detection system 50. Typically, the detection system 50 includes an array of individual detectors.

In the illustrated embodiment, the x-ray source 20 is connected to the kV meter 55, which includes a principal detector 52, and an auxiliary detector 54. The auxiliary detector 54, but not the principal detector 52, is covered by an absorber 56, which absorbs lower energy x-ray photons much more strongly, as compared to higher energy x-ray photons. The absorber 56 thus prevents a large fraction of the lower energy x-ray photons in the incident beam from being detected. In a preferred embodiment of the invention, the absorber 56 is made of a material chosen to optimize the sensitivity of the ratio of the first and second intensity magnitudes to voltage fluctuations. The material forming the absorber may include, but is not limited to, copper, molybdenum, and tungsten. Preferably, both the principal 52 and the auxiliary 54 detectors are semiconductor detectors, which have a superior stability, as compared to scintillator detectors.

The x-ray intensity is measured in two x-ray beams. A first beam is detected by the principal detector 52, which is exposed to all the x-ray photons in the first beam. The principal detector 52 measures a first intensity magnitude for the first beam. A second beam is detected by the auxiliary detector 54, after a large fraction of the x-ray photons (corresponding to the lower-energy range of photons) has been removed. The auxiliary detector 54 measures a second intensity magnitude for the second beam. The ratio between the first and the second intensity magnitudes is a known, sensitive and stable (essentially time-independent) function of the voltage provided to the x-ray source 20. Accordingly, this ratio can be used to detect fluctuations in the voltage. Other known, measurable functions of the intensity magnitudes can also be used.

The signals generated by the detecting system 50 are indicative, among other things, of the differences in attenuation of the x-rays along the different paths taken by the rays, as they traverse the slice 40 of the target object. The attenuation of an x-ray beam is proportional to the natural logarithm of the ratio of the incident beam intensity to the transmitted beam intensity. The attenuation characteristics of an object or a material are energy dependent, i.e. vary as a function of the x-ray energy. In some materials, the attenuation characteristics may vary at high rates as a function of x-ray energy, while in other materials the attenuation characteristics may be less affected by variations in x-ray energy.

In particular, it is known that when a monochromatic x-ray beam of energy E passes through an object of uniform density, it is attenuated according to the formula:

$$I = I_0 e^{-\mu L}, \quad (1)$$

where $I_0$=the incident x-ray intensity,
I=the transmitted x-ray intensity,
L=the path length through the uniform density object, and
$\mu$=the attenuation coefficient at energy E, where the attenuation coefficient in general varies with E. The CT numbers of a target object can be determined using the attenuation of the x-rays transmitted therethrough, because the CT numbers of a target object are related in a known way to the attenuation coefficients of the target object at a given energy.

In the exemplary embodiment illustrated in FIG. 1, the detection system 50 is connected to the data acquisition system 82 and the image processor 70. The detection system 50 transmits the detection signals to the data acquisition system 82, which in turn transmits the signals to the image processor 70. The analog data coming from the detection system 50 are acquired and digitized by the data acquisition system 82. The data acquisition system 82 includes at least one analog-to-digital converter 83 for converting the analog detection signals generated by the detecting system 50 into digitized data.

The digitized data are used by the image processor 70 to calculate the CT numbers, according to well known CT image processing techniques, such as filtered back projection. The image processor 70 generates a CT image of the target object using these known techniques. The image processor 70 may also include an image memory unit 72, and an image display unit 74, such as a monitor screen, for displaying the final CT image of the target object.

Each cross-sectional slice 40 of the target object is viewed as being composed of many individual volume elements. A CT number is calculated for each volume element, and is indicative of the x-ray attenuation characteristics pertaining to that volume element. In order to accurately reconstruct a CT image of the target object, therefore, it is critical that the CT numbers be determined accurately.

In order for the CT numbers to be accurately determined, the energy spectrum of the x-rays must remain constant, once the CT system has been calibrated. The energy spectrum of the x-rays strongly depends on the voltage provided to the x-ray source 20. Accordingly, fluctuations in voltage, caused for example by voltage source drift or other long term degradation of the voltage source 30, cause undesirable fluctuations in the CT numbers, undermining the accuracy of the CT numbers calculated by the CT system 10.

Figure 2A:
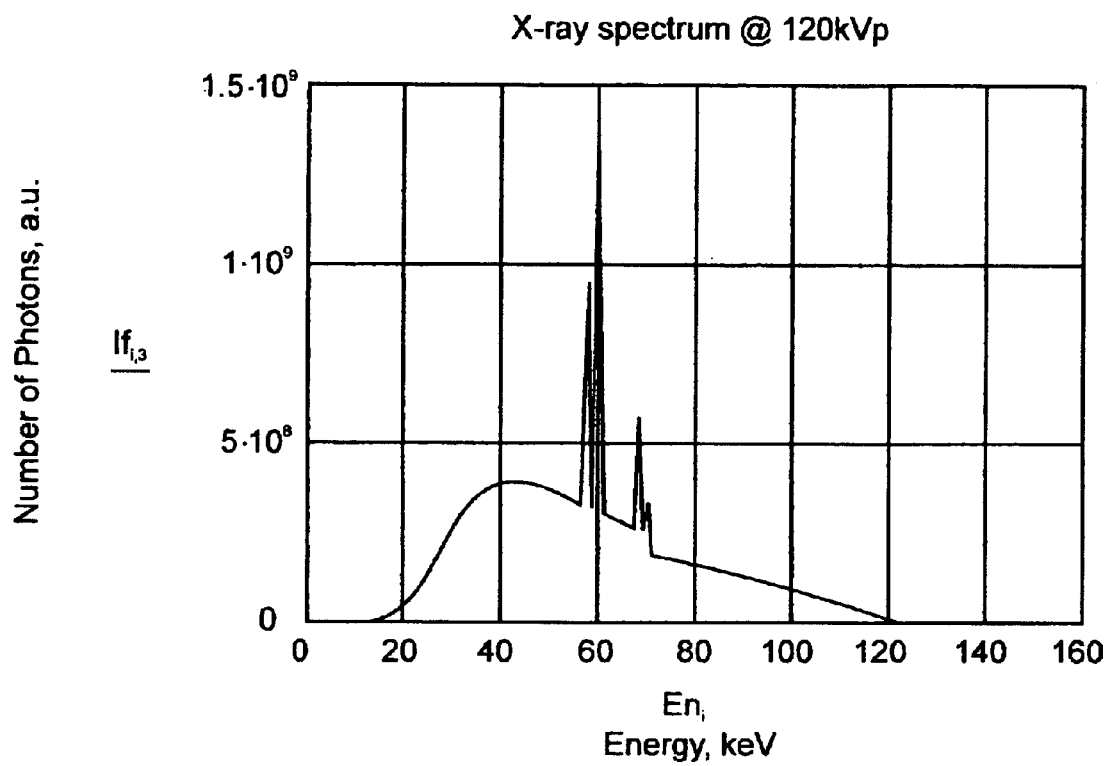
FIG. 2(a) illustrates an exemplary x-ray energy spectrum.
Figure 2B:
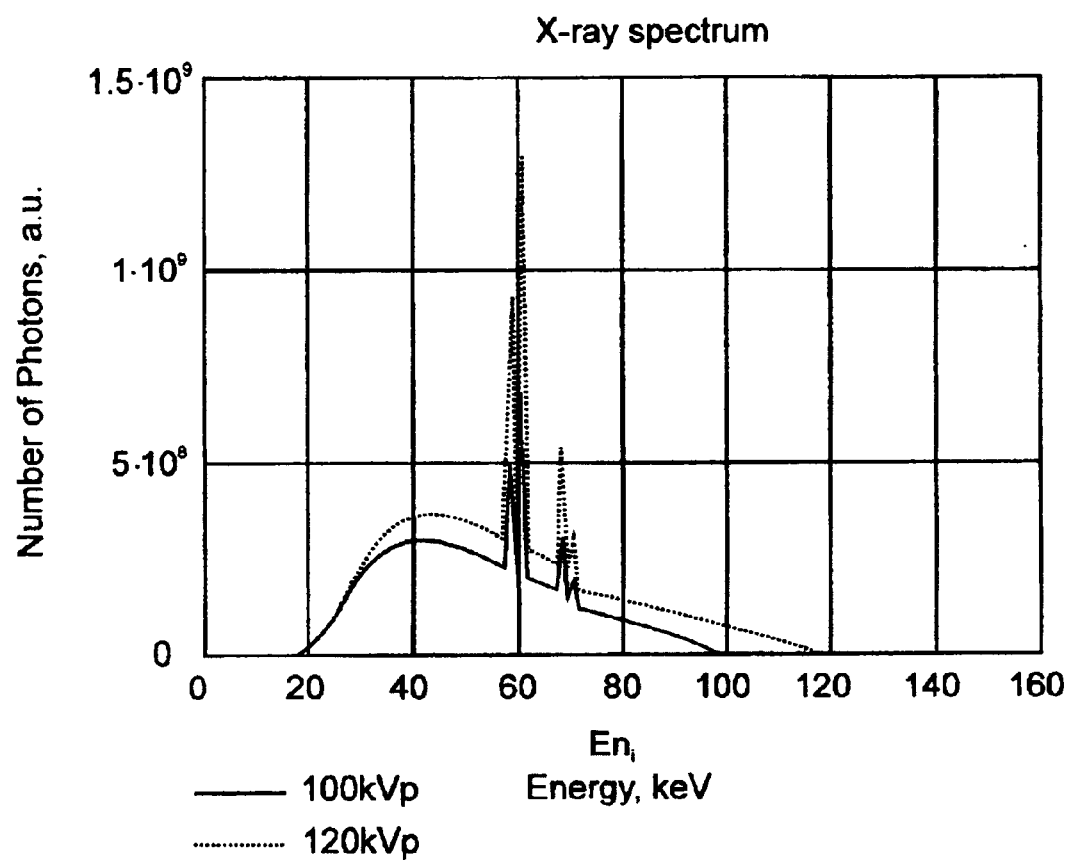
FIG. 2(b) illustrates the change in the x-ray energy spectrum, caused by a change in the electron accelerating voltage provided to an x-ray source. The two spectra shown in FIG. 2(b) are normalized to the number of electrons incident on the x-ray target in the x-ray tube.

FIG. 2(a) illustrates an exemplary x-ray spectrum, i.e. an exemplary graph of the x-ray intensity as a function of the energy. FIG. 2(b) illustrates the sensitive dependence of the x-ray spectrum on the x-ray source voltage. In FIG. 2(a), the x-ray spectrum of tungsten is shown. It is known that x-rays are produced when the incident electrons, interacting with the target nuclei and with the electrons surrounding the target nuclei, are decelerated and eventually brought to rest. The spectrum of the emitted x-rays thus depends, among other things, on the accelerating voltage that accelerates the beam of electrons striking the target. As seen from FIG. 2(a), the x-ray spectrum includes a continuous bremsstrahlung spectrum, as well as spectral lines characteristic of the material forming the target, and of the transitions between bound electron energy levels of the material.

The change in the x-ray spectrum, which occurs when the x-ray source voltage is changed, can be observed in FIG. 2(b). In particular, FIG. 2(b) illustrates the x-ray emission spectra for a tungsten target when the x-ray source is operated at two different voltages, namely at 120 kV (dotted spectrum), and at 100 kV (solid spectrum). The two spectra shown in FIG. 2(b) are normalized to the number of electrons incident on the x-ray target. Any change in the accelerating voltage between the cathode and the target in the x-ray source results in a corresponding change in the energy with which the electrons strike the focal spot. As illustrated in FIG. 2(b), a change in the acceleration voltage results in a total x-ray output variation approximately proportional to the square of the voltage, with a corresponding shift in the peak x-ray photon energy. As expected, the maximum x-ray photon energy is equal to the maximum energy of the incident electrons. FIG. 2(b) shows that for a given number of electrons, the total number of x-rays are much greater for an accelerating voltage of 120 kV, as compared to an accelerating voltage of 100 kV. FIG. 2(b) also shows that the average energy moves toward higher energies more rapidly, as compared to the maximum energy.

Figure 3A:
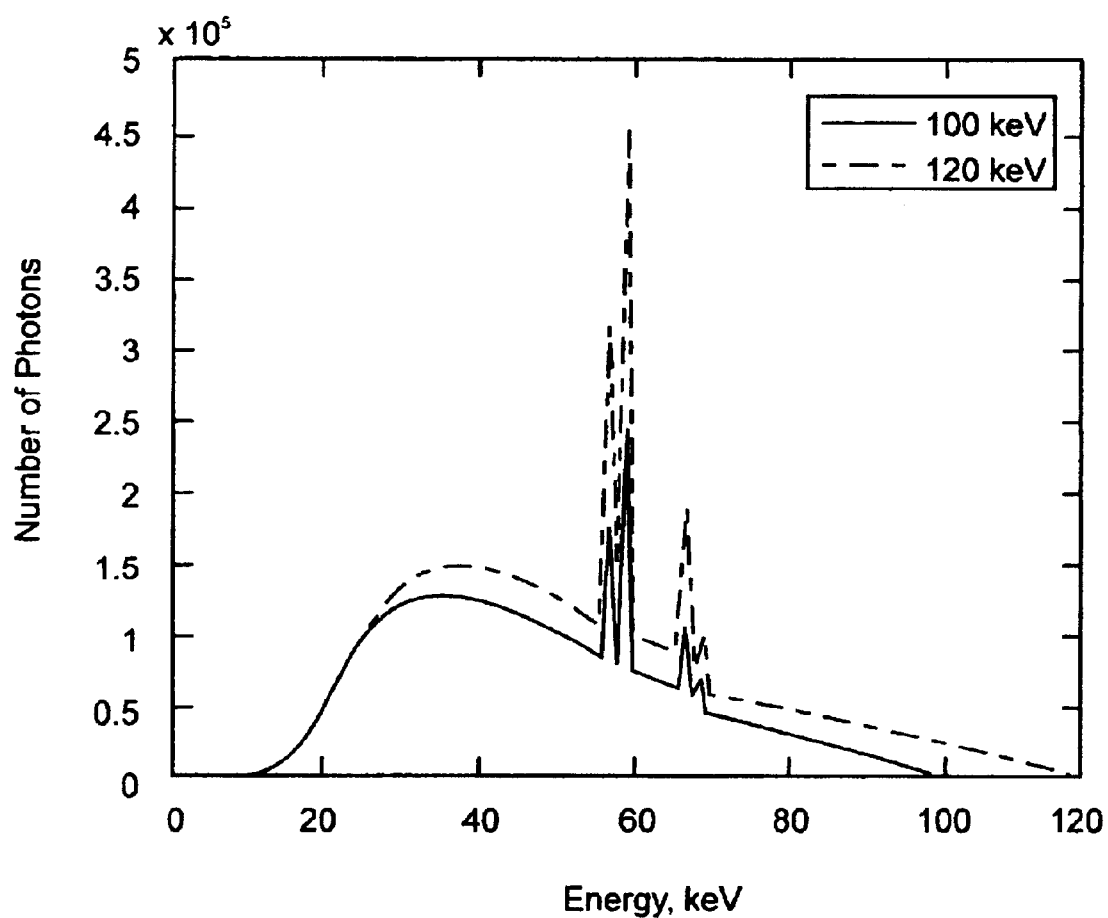
FIGS. 3(a) and 3(b) illustrate the spectra of x-ray photons obtained from i) a principal detector and ii) an auxiliary detector having an absorber that preferentially absorbs low energy x-ray photons, at two different x-ray source voltages, namely 100 keV and 120 keV. The four spectra illustrated in FIGS. 3(a) and 3(b) all result from the same number of electrons impinging upon the x-ray target.
Figure 3B:
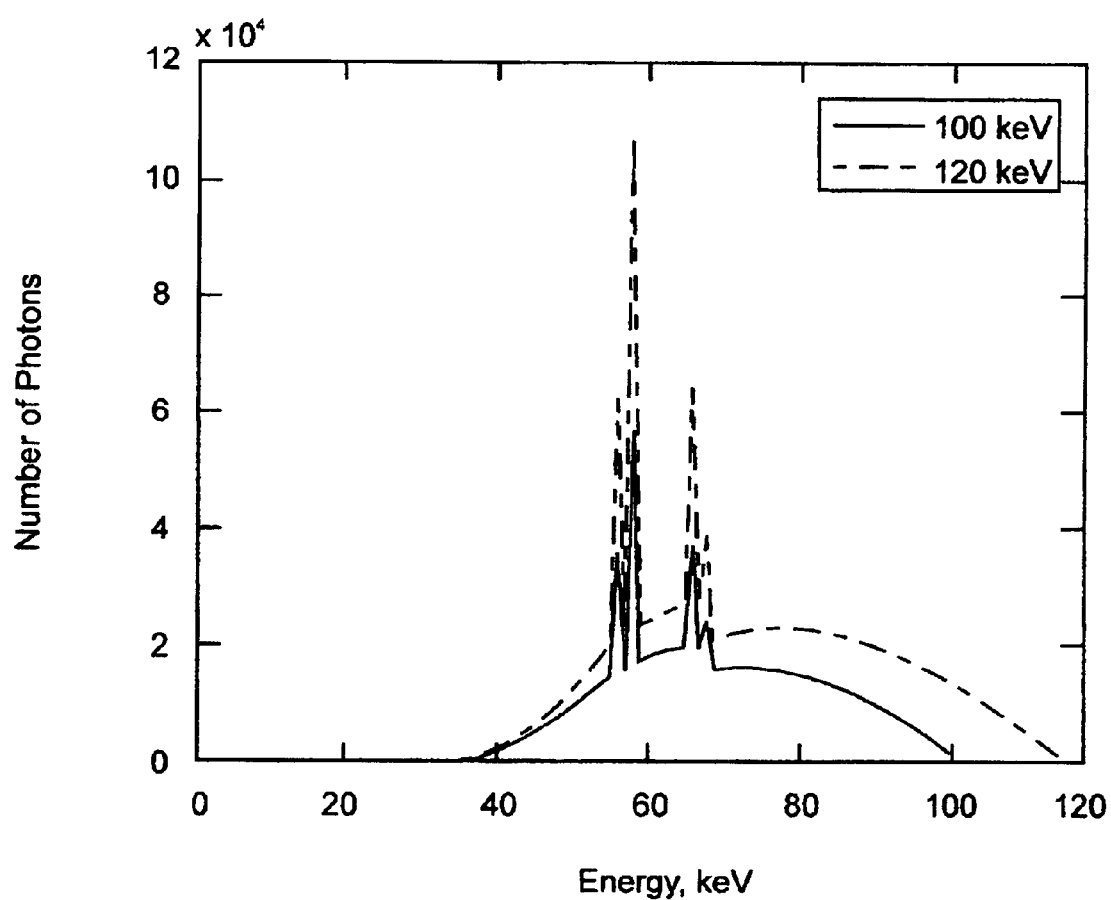

FIGS. 3(a) and 3(b) illustrate the x-ray energy spectra as respectively obtained from the principal detector (spectrum shown in FIG. 3(a)), and from the auxiliary detector (spectrum shown in FIG. 3(b)). The number of x-ray photons per energy interval is plotted as a function of the x-ray photon energy. In both figures, the solid curve represents the spectrum at an x-ray source voltage level of 100 keV, whereas the dotted curve represents the spectrum at an x-ray source voltage level of 120 keV. It can be seen that the total intensity is much less in the auxiliary detector (as shown in FIG. 3(b)), as compared to the total intensity in the principal detector (as shown in FIG. 3(a)).

As shown in FIGS. 3(a) and 3(b), the spectrum from the auxiliary detector has a greatly decreased contribution from the lower energy x-ray photons, because a large portion of the lower energy incident x-ray photons has been removed from the beam. The spectral curves all terminate at the respective source voltages, 120 keV and 100 keV, since no x-ray photon can have an energy greater than the maximum kinetic energy of the incident electrons, as represented by the source voltage.

The photon flux illustrated in the four curves shown in FIGS. 3(a) and 3(b) result from the same number of electrons impinging on the anode, for all four curves. The first and second intensity magnitudes are obtained as integrals under the respective spectral curves. It can be seen from the illustrated curves that the ratio of the areas under the dotted curves is very different, as compared to the ratio of the areas under the solid curves. The strong dependence of the ratio of the first and second intensity magnitudes on the respective values of the source voltage, i.e. 100 keV and 120 keV, can thus be observed. The relationship between the measured ratio of intensity magnitudes and the x-ray source voltage is only a function of the physical characteristics of the principal and auxiliary detectors, which do not change over time.

As explained earlier, the primary aspect of this invention is to maintain the x-ray source voltage stable against fluctuations, in order to accurately determine the CT numbers. Referring back to FIG. 1, the feedback controller 90 (including the processing unit 99) is provided in the present invention in order to maintain the voltage across the x-ray source 20 constant, thereby stabilizing the calculations of CT numbers by the CT system 10.

In a preferred embodiment of the invention, the voltage V produced by the power supply 30 is controlled by an input command $V_{control}$ from the feedback controller 90. $V_{control}$ may either be an analog signal, or a digital signal. The ratio between the voltage V provided by the power supply 30 and the input command $V_{control}$, denoted as K for convenience, is dependent upon the characteristics of numerous electronic components. K therefore generally drifts with time. In the present invention, the adverse effects resulting from the drift in K are avoided by continuously adjusting the command $V_{control}$ from the controller 90, as K changes or drifts with time.

In operation, an initial calibration step is performed for the CT system 10, during which the CT number of one or more samples having a known CT number value is measured. The x-ray source voltage provided to the x-ray source in the CT system 10 is adjusted until the measured value of the CT number of the sample matches the known CT number. The resulting magnitude of the x-ray source voltage is measured by the kV meter. This magnitude serves as a reference level $V_{control}$ for feedback control. Alternately, the kV meter may measure the x-ray energy, instead of measuring the x-ray source voltage, and the value of the x-ray energy may serve as a reference for feedback control.

In a preferred embodiment, the kV meter monitors the changes in $V_{measured}$ from the reference level $V_{reference}$ established during calibration, by measuring the first and the second intensity magnitudes generated by the principal detector 52 and the auxiliary detector 54. As explained earlier, a minimal change or fluctuation in voltage results in a large change in the ratio of the intensity magnitudes, or in some other known and measurable functions of the intensity magnitudes. The ratio of the intensity magnitudes may be calibrated by measuring the voltage supplied to the x-ray source electronically, and constructing a table of voltages and corresponding ratios. The voltage control signal 92 is continuously adjusted based on the ratio of the magnitudes.

During subsequent measurements of CT numbers by the CT system 10, the feedback controller 90 continuously adjusts the voltage control signal 92 that it sends to the voltage source 30, so as to keep the measured x-ray source voltage fixed at the reference level established during calibration. The absolute magnitude of this reference level need not even be known, as long as the voltage control signal 92 is continually adjusted so as to keep the measured x-ray source voltage or the measured x-ray energy unchanged with respect to the reference level.

In a nutshell, the process of adjusting the voltage control signal 92, in a preferred embodiment of the present invention, starts with the step of measuring the ratio K between the voltage V from the power supply 30 and the command signal $V_{control}$. The ratio K is measured by measuring the voltage V from the power supply 30, and dividing by the initial voltage control signal, $V_{control}$:

$$K_{measured}=V_{measured}/V_{control}.$$

$K_{measured}$ is then used to generate a new command signal, $V_{control, new}$. This procedure is repeated continuously, in order to keep the measured x-ray source voltage constant after the calibration step.

More specifically, the process of continuously adjusting the voltage control signal 92 ($V_{control}$) includes the following steps, in a preferred embodiment of the invention. First, the CT system 10 is turned on. At this point, the voltage command signal from the controller 90 has an initial value, $V_{init}$. Next, the processing unit 99 in the controller looks up a nominal value $K_{nominal}$ of the ratio between the voltage from the power supply 30 and the command signal from the controller 90. Using the values of $V_{init}$ and $K_{nominal}$, the processing unit 99 calculates a control signal $V_{control}$, and provides it to the controller 90, where $$V_{control}=V_{init}/K_{nominal}. \quad (1)$$

The feedback controller 90 sends the voltage control signal 92 to the voltage source 30.

The kV meter 55 then measures the voltage provided to the x-ray source 20 by the voltage source 30. The value of the voltage, as measured by the kV meter, is denoted $V_{measured}$, for convenience. Next, $V_{measured}$ is used to generate a measured value $K_{measured}$ for K, where:

$$K_{measured}=V_{measured}/V_{control}, \quad (2)$$

and $V_{control}$ has previously been determined, according to Equation (1).

Using $K_{measured}$, the processing unit 99 computes a new value $V_{control, new}$ for the voltage control signal, where $V_{control, new}$ is determined by:

$$V_{control, new}=V_{init}/K_{measured} \quad (3)$$

The system 10 sends the new control signal $V_{control, new}$ to the controller 90. The steps described in the paragraphs following equations (1) and (2) above are then repeated, until $V_{measured}$ equals the reference level $V_{reference}$, established during calibration.

The feedback controller 90 continuously adjusts the voltage control signal 92 to the voltage source 30, using the measured ratio $K_{measured}$ as a sensitive way of detecting any change in voltage. Since the measurement is ratiometric and the electronics are all working at low voltages, the measurement is intrinsically very stable. The x-ray source voltage is thus kept constant at a reference level $V_{reference}$ corresponding to the x-ray source voltage level when the CT number as measured by the CT system 10 is essentially equal to the known CT number value of a sample.

Preferably, any deviation of the voltage from the reference magnitude is maintained to less than about 0.03%. Since the CT system 10 is continuously measuring and adjusting the voltage, the CT system 10 is able to produce an inherently stable determination of the CT numbers, which are dependant on that voltage. Preferably, the variation in the determined values of CT numbers is reduce to less than about 0.1%.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method of stabilizing the calculation of CT (computed tomography) numbers by a CT system, the CT system including an x-ray source for generating x-rays in response to a voltage supplied by a voltage source, the method comprising:
   a) calculating the CT number of a sample having a known CT number value;
   b) adjusting the voltage supplied by the voltage source to a reference level for which the calculation in step (a) yields said known CT number value; and
   c) measuring the energy spectrum of the x-rays generated by the x-ray source;
   d) adaptively regulating the voltage based on the spectrum measured in step (c), so as to prevent any deviation in the voltage from said reference level determined in step (b); and
   e) maintaining the voltage substantially constant at said reference level by repeating steps (c) and (d) during subsequent CT number measurements by said CT system.

2. A method according to claim 1,
   A. wherein measuring the energy spectrum of the x-rays in step (c) comprises:
      i) using a principal detector to detect x-rays emitted by said x-ray source so as to generate a first intensity magnitude;
      ii) using an auxiliary detector to detect x-rays emitted by said x-ray source so as to generate a second intensity magnitude, said auxiliary detector including an absorber that preferentially absorbs x-ray photons having a relatively low energy; and
   B. wherein regulating the voltage in step (d) comprises:
      (i) generating a control signal proportional to a known function of said first and second intensity magnitudes; and
      (ii) adjusting said voltage based on said control signal.

3. A method according to claim 2, wherein said absorber is made of a material adapted to optimize the sensitivity of said known function to fluctuations in said voltage from said reference level.

4. A method according to claim 3, wherein said absorber is selected from the group consisting of copper, molybdenum, and tungsten.

5. A method according to claim 2, wherein said known function of said first and second intensity magnitudes comprises a ratio of the first and second intensity magnitudes.

6. A method according to claim 1, wherein regulating the voltage in step (d) comprises providing to the voltage source a voltage control signal proportional to the deviation in voltage from said reference level.

7. A method according to claim 1, wherein the variation in the values of CT numbers measured by said CT system is reduced to less than about 0.1%.

8. A method according to claim 1,
   wherein the deviation of said voltage from said reference level is maintained to less than about 0.03%.

9. A method according to claim 1, further comprising:
   i) recording, after step (b), the measured x-ray energy value resulting from the adjustment of said voltage in step (b); and
   ii) in step (d), regulating the voltage so that the measurement of the x-ray energy in step (c) yields the value recorded in step (i).

10. A method according to claim 1, wherein said sample having a known CT number value comprises water.

11. A method of stabilizing the measurement of CT numbers by a CT system, the CT system including an x-ray source for generating x-rays in response to a voltage provided by a voltage source, the method comprising:
   a) establishing a reference level for said voltage by adjusting the voltage to a value for which calculation by said CT system of the CT number of a sample having a known CT number value yields said known CT number value;
   b) using a principal detector to detect x-rays generated by said x-ray source so as to generate a first intensity magnitude;
   c) using an auxiliary detector to detect x-rays generated by said x-ray source so as to generate a second intensity magnitude, wherein said auxiliary detector includes an absorber that preferentially absorbs x-ray photons having a relatively low energy;
   d) generating a voltage control signal, and providing said voltage control signal to said voltage source, so as to maintain said voltage substantially constant at said reference level, thereby substantially reducing in said CT system a variation in the calculated values of CT numbers;
wherein said voltage control signal is proportional to a known function of said first and second intensity magnitudes.

12. A CT system, comprising:
   a) an x-ray source for generating x-rays in response to a voltage provided by a voltage source;
   b) a detection system for detecting x-rays generated by said x-ray source and transmitted through a target object;
   c) a kV meter for measuring an energy spectrum of x-rays generated by said x-ray source;
   d) a processor for calculating the CT numbers of said target object; and
   (e) a feedback controller for providing to the voltage source a voltage control signal;
wherein the energy spectrum measured by said kV meter is used to adjust said voltage control signal so as to maintain said voltage substantially constant at a reference level established during calibration, and
wherein said reference level is the voltage level at which calculation by said CT system of the CT number of a sample having a known CT number value yields the correct known CT number value.

13. A CT system according to claim 12,
   wherein said kV meter includes a principal detector for detecting x-rays generated by said x-ray source so as to generate a first intensity magnitude, and an auxiliary detector for detecting x-rays generated by said x-ray source so as to generate a second intensity magnitude, said auxiliary detector including an absorber that preferentially absorbs x-ray photons having a relatively low energy; and
   wherein said voltage control signal is proportional to a known function of said first and second intensity magnitudes.

14. A CT system according to claim 13, wherein at least one of said principal detector and said auxiliary detector comprises a semiconductor detector.

15. A CT system according to claim 13, wherein said known function of said first and second intensity magnitudes comprises a ratio of said first and second intensity magnitudes.

16. A CT system according to claim 12, wherein said detector system includes an array of detectors.

17. A CT system for performing stabilized CT number measurements, said CT system comprising:
   a) an x-ray source for generating x-rays in response to a voltage provided by a voltage source;
   b) a detection system for detecting x-rays emitted by said x-ray source and transmitted through a target object;
   c) a kV meter, comprising:
      i) a principal detector for detecting x-rays generated by said x-ray source so as to generate a first intensity magnitude;
      ii) an auxiliary detector for detecting x-rays generated by said x-ray source so as to generate a second intensity magnitude, said auxiliary detector including an absorber that preferentially absorbs x-ray photons having a relatively low energy;
   d) a processor for calculating CT numbers of said target object so as to reconstruct a CT image of said target object; and
   e) a feedback controller for providing to the voltage source a voltage control signal;
   wherein said voltage control signal is adjusted as a function of a ratio of said first and second intensity magnitudes so as to maintain said voltage substantially constant at a reference level established during calibration, thereby substantially reducing in said CT system a variation in the measured values of CT numbers; and
   wherein said reference level is the magnitude of the voltage at which calculation by said CT system of a sample having a known CT number value yields the correct known CT number value.

18. An apparatus for stabilizing CT number calculations by a CT system having an x-ray source for generating x-rays in response to a voltage provided by a voltage source, the apparatus comprising:
   a) a kV meter for measuring a spectrum of x-rays generated by said x-ray source so that the voltage provided by the voltage source can be adjusted to a reference level at which the CT number of a sample as measured by said CT system is substantially equal to a known CT number value; and
   b) a feedback controller for providing to the voltage source a voltage control signal based on said measured x-ray spectrum so that the voltage can be adjusted in response to said control signal so as to maintain the voltage constant at said reference level, thereby substantially reducing a variation in the calculated values of the CT numbers of a target object, as determined by said CT system.

19. An apparatus for stabilizing CT number calculations in a CT system having an x-ray source for generating x-rays in response to a voltage provided by a voltage source, the apparatus comprising:
   a) a principal detector for detecting x-rays generated by said x-ray source so as to generate a first intensity magnitude;
   b) an auxiliary detector having an absorber that preferentially absorbs x-rays photons having a relatively low energy, the auxiliary detector being adapted to detect x-rays generated by said x-ray source so as to generate a second intensity magnitude; and
   c) a feedback controller for providing to the voltage source a voltage control signal;
   wherein said voltage control signal is adaptively adjusted, based on a predetermined function of said first intensity magnitude and said second intensity magnitude, so as to maintain the voltage provided to the x-ray source constant at a reference level for which the calculation by said CT system of the CT number of a sample having a known CT number value yields the correct known CT number value.

20. An apparatus according to claim 19, wherein said predetermined function is a ratio between said first intensity magnitude and said second intensity magnitude.

* * * * *